(12) United States Patent
Baek et al.

(10) Patent No.: US 10,181,072 B2
(45) Date of Patent: Jan. 15, 2019

(54) ROLLABLE BIOMETRIC MEASURING DEVICE

(71) Applicant: QUALCOMM Incorporated, San Diego, CA (US)

(72) Inventors: David Boettcher Baek, San Diego, CA (US); Aiman Abdel-Malek, La Jolla, CA (US); Muhammed Sezan, Los Gatos, CA (US); Lars Lading, Roskilde (DK); Eugene Dantsker, San Diego, CA (US)

(73) Assignee: QUALCOMM Incorporated, San Diego, CA (US)

( * ) Notice: Subject to any disclaimer, the term of this patent is extended or adjusted under 35 U.S.C. 154(b) by 65 days.

(21) Appl. No.: 15/077,126

(22) Filed: Mar. 22, 2016

(65) Prior Publication Data

US 2017/0277937 A1  Sep. 28, 2017

(51) Int. Cl.
*A61B 5/00* (2006.01)
*G06K 9/00* (2006.01)
*A61B 5/02* (2006.01)
*A61B 5/0205* (2006.01)
*A61B 5/022* (2006.01)
*A61B 5/1172* (2016.01)
*A61B 5/1455* (2006.01)
(Continued)

(52) U.S. Cl.
CPC ........ *G06K 9/00087* (2013.01); *A61B 5/0002* (2013.01); *A61B 5/0205* (2013.01); *A61B 5/02007* (2013.01); *A61B 5/02233* (2013.01); *A61B 5/02416* (2013.01); *A61B 5/0535* (2013.01); *A61B 5/1172* (2013.01); *A61B 5/14551* (2013.01); *A61B 5/4875* (2013.01); *A61B 5/6826* (2013.01); *G06K 9/00013* (2013.01); *G06K 2009/00932* (2013.01); *G06K 2009/00939* (2013.01)

(58) Field of Classification Search
None
See application file for complete search history.

(56) References Cited

U.S. PATENT DOCUMENTS 5,452,717 A 9/1995 Branigan et al.
5,539,706 A * 7/1996 Takenaka ........... A61B 5/02422
368/10

(Continued)

FOREIGN PATENT DOCUMENTS

CN  104398246 A  3/2015
CN  105011939 A  11/2015
(Continued)

OTHER PUBLICATIONS

International Search Report and Written Opinion—PCT/US2017/018949—ISA/EPO—dated May 24, 2017.

*Primary Examiner* — Ankit D Tejani
(74) *Attorney, Agent, or Firm* — Bala Ramasamy; Kilpatrick Townsend & Stockton

(57) ABSTRACT

A biometric measuring device for obtaining biometric measurements on a limb or digit, such as a finger. The biometric measuring device may include a rollable sleeve that is rollable along a longitudinal axis of the limb or digit and multiple biometric sensors attached to the rollable sleeve such that the biometric sensors are positioned on the rollable sleeve to enable the sleeve to be rolled.

30 Claims, 10 Drawing Sheets

(51) Int. Cl.
*A61B 5/024* (2006.01)
*A61B 5/053* (2006.01)

(56) References Cited

U.S. PATENT DOCUMENTS

| | | | | |
|---|---|---|---|---|
| 5,650,982 | A * | 7/1997 | Takenaka | A61B 5/02422 368/10 |
| 6,155,120 | A * | 12/2000 | Taylor | A61B 5/1036 73/862.046 |
| 6,280,390 | B1 | 8/2001 | Akselrod et al. | |
| 7,601,123 | B2 | 10/2009 | Tweed et al. | |
| 7,674,231 | B2 | 3/2010 | McCombie et al. | |
| 8,672,854 | B2 | 3/2014 | McCombie et al. | |
| 2001/0047194 | A1* | 11/2001 | Thompson | A61B 5/0031 607/59 |
| 2003/0190062 | A1* | 10/2003 | Noro | A61B 5/022 382/124 |
| 2007/0038048 | A1 | 2/2007 | Gerder | |
| 2007/0276262 | A1* | 11/2007 | Banet | A61B 5/02255 600/485 |
| 2008/0081963 | A1* | 4/2008 | Naghavi | A61B 5/01 600/301 |
| 2009/0043180 | A1 | 2/2009 | Tschautscher et al. | |
| 2011/0015498 | A1 | 1/2011 | Mestrovic et al. | |
| 2013/0137943 | A1* | 5/2013 | Pinto Rodrigues | A61B 5/01 600/301 |
| 2014/0171767 | A1* | 6/2014 | Hotaling | A61B 8/06 600/323 |
| 2014/0330087 | A1 | 11/2014 | Succi et al. | |
| 2015/0051501 | A1* | 2/2015 | Dugan | A61B 5/02 600/483 |
| 2015/0223716 | A1* | 8/2015 | Korkala | A61B 5/0245 600/393 |
| 2015/0366504 | A1* | 12/2015 | Connor | A61B 5/6804 600/301 |
| 2016/0073886 | A1* | 3/2016 | Connor | G09B 19/0092 600/475 |
| 2017/0119293 | A1 | 5/2017 | Matsui | |

FOREIGN PATENT DOCUMENTS

| | | |
|---|---|---|
| JP | 2006087516 A | 4/2006 |
| KR | 20120096227 A | 8/2012 |
| WO | 2015177867 A1 | 11/2015 |

* cited by examiner

ROLLABLE BIOMETRIC MEASURING DEVICE

BACKGROUND

Devices for measuring cardiovascular properties suffer from the problem that the measurement itself may interfere strongly with the state of the subject, thereby leading to erroneous results. For example, current cuff-based methods for obtaining blood pressure measurements may impart a significant physiological impact. In current cuff-based methods, blood pressure measurements are obtained by constricting an artery to the extent that blood flow is completely blocked and then slowly releasing the constriction. Constricting the artery affects pulse pressure propagation and pulse pressure shapes. Further, the diastolic pressure is derived from measurements obtained when the transmural pressure (i.e., pressure difference between the outside and the inside of an artery) is close to zero, which implies those measurements are made under conditions that are far from normal.

In addition, traditional methods based on inflatable cuffs and measurements performed in a clinical environment may have strong psychological effects causing changes in a patient's blood pressure. For example, the psychological effects of being in a clinical environment may cause an elevation in the patient's blood pressure. The phenomenon is commonly called "white coat syndrome" or "white coat hypertension." In an additional example, a patient's blood pressure may be elevated during normal daily activities but not in a clinical environment. This phenomenon is commonly called "masked hypertension."

Additionally, blood pressure often exhibits considerable variability over time. Thus, identifying diurnal or other temporal variations in blood pressure may be important for proper diagnosis of various cardiovascular issues, including hypertension. It has also been shown that performing ambulatory blood pressure measurements may be beneficial for improved diagnosis by facilitating measurements over longer time periods and avoiding the psychological effects typical in clinical environments.

SUMMARY

Various embodiments include a biometric measuring device for obtaining biometric measurements on a limb or digit, such as a finger. In various embodiments, the biometric measuring device may include a rollable sleeve that is rollable along a longitudinal axis of the limb or digit and multiple biometric sensors attached to the rollable sleeve such that the biometric sensors are positioned on the rollable sleeve to enable the sleeve to be rolled. In some embodiments, the biometric sensors are positioned to further enable the biometric sensors to be in proximity with the limb or digit when the rollable sleeve is rolled out over the longitudinal axis of the limb or digit. In some embodiments, the biometric sensors are positioned to further enable biometric information to be captured regardless of orientation of the rollable sleeve on the limb or digit. In some embodiments, the biometric sensors may include an optical sensor, an ultrasonic sensor, and a bio-impedance sensor, or any combination thereof.

In some embodiments, the biometric measuring device may include a fingerprint sensor attached to the rollable sleeve at a location that enables fingerprint data of the subject to be captured when the rollable sleeve is rolled out on a digit. In some embodiments, the biometric measuring device may include a processor coupled to the fingerprint sensor and the processor may be configured to verify the identity of the subject based on the fingerprint data captured by the fingerprint sensor and associate the obtained biometric measurements with the identity of the subject.

In some embodiments, the biometric measuring device may include a pressure sensor attached to the rollable sleeve, with the pressure sensors configured to determine a counter pressure applied to the limb or digit by the rollable sleeve. In some embodiments, the pressure sensor may include a capacitive material strip, a piezo resistive film, or a strain gauge.

In some embodiments, the rollable sleeve may be configured to roll out over the limb or digit starting from an at least partially rolled up state in which at least a portion of the rollable sleeve containing the biometric sensors is at least partially rolled up defining an annular opening.

In some embodiments, the rollable sleeve may be made of an elastic material and at least one of the biometric sensors may be embedded within the elastic material of the rollable sleeve. In some embodiments, the rollable sleeve may include a moulded structure and the biometric sensors may be embedded in or attached to the moulded structure of the rollable sleeve. In some embodiments, the rollable sleeve may include a material that provides a constant counter pressure when the rollable sleeve is rolled out on the limb or digit. In some embodiments, the rollable sleeve may be waterproof.

In some embodiments, the biometric measuring device may further include a processor coupled to the biometric sensors and the processor may be configured to determine one or more biometric measurements based on outputs received from the biometric sensors. In some embodiments, the biometric measuring device may further include a transceiver coupled to the processor, and the transceiver may be configured to transmit the one or more biometric measurements to a remote device.

In some embodiments, the biometric measuring device may further include a Faraday cage attached to the rollable sleeve and the Faraday cage may be configured to electrically shield the biometric sensors.

Further embodiments include methods of measuring a biometric property of a subject using a biometric measuring device that may include a rollable sleeve and biometric sensors attached to the rollable sleeve such that the biometric sensors are positioned on the rollable sleeve to enabled the sleeve to be rolled. Some embodiments may include receiving output signals from the biometric sensors attached to the rollable sleeve when the rollable sleeve is deployed on a limb or digit of the subject, such as a finger, and processing the output signals to obtain one or more biometric measurements. In some embodiments, processing the output signals to obtain one or more biometric measurements may be performed in a processor coupled to the biometric sensors. In some embodiments, processing the output signals to obtain one or more biometric measurements may include transmitting the output signals to a computing device separate from the biometric measuring device, and processing the output signals in a processor of the computing device to obtain the one or more biometric measurements.

Some embodiments may further include capturing fingerprint data of the subject by a fingerprint sensor attached to the rollable sleeve at a location that enables fingerprint data of the subject to be captured when the rollable sleeve is deployed on the digit of the subject. Some embodiments may further include verifying an identify of the subject based on the fingerprint data captured by the fingerprint sensor and associating the obtained biometric measurements with the identity of the subject.

Some embodiments may further include determining a counter pressure applied to the limb or digit by the rollable sleeve based on an output of a pressure sensor attached to the rollable sleeve.

Further embodiments include a biometric measuring device for obtaining biometric measurements on a limb or digit of a subject including a rollable sleeve that is rollable along a longitudinal axis of the limb or digit and multiple means for obtaining biometric measurements attached to the rollable sleeve such that the multiple means for obtaining biometric measurements are positioned on the rollable sleeve to enable the sleeve to be rolled.

BRIEF DESCRIPTION OF THE DRAWING

The accompanying drawings, which are incorporated herein and constitute part of this specification, illustrate exemplary embodiments of the claims, and together with the general description given above and the detailed description given below, serve to explain the features of the claims.

DETAILED DESCRIPTION

Figure 1A:
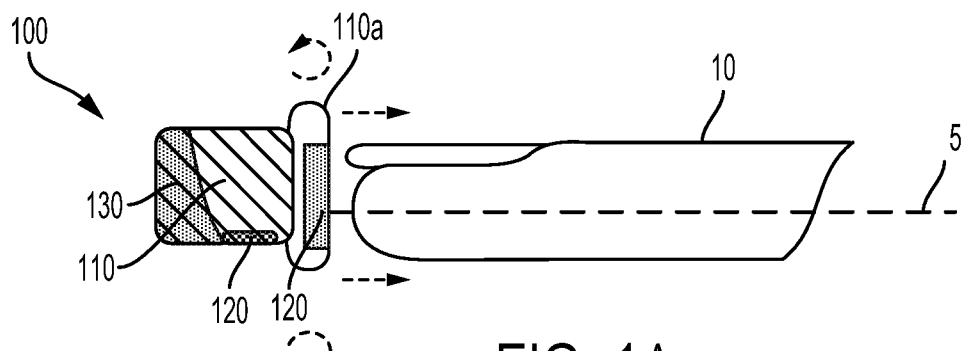
FIGS. 1A, 1B, and 1C illustrate a biometric measuring device for obtaining various biometric measurements according to some embodiments.

Various embodiments will be described in detail with reference to the accompanying drawings. Wherever possible, the same reference numbers will be used throughout the drawings to refer to the same or like parts. References made to particular examples and implementations are for illustrative purposes, and are not intended to limit the scope of the claims.

The term "cardiovascular properties" is used herein as a general term to refer to characteristics of a cardiovascular system including, but not limited to, arterial beat-to-beat distension, pulse transit time (PTT), pulse wave velocity (PWV), mean arterial cross-sectional area, arterial stiffness, heart rate, heart rate variability, oxygen level (e.g., $SpO_2$), blood flow rate, body water index, pulse shape, blood flow, and blood pressure.

The term "biometric measuring device" is used herein to refer to a physical apparatus that includes a rollable sleeve that is rollable along a longitudinal axis of a limb or digit (e.g., a finger) and biometric sensors attached to the rollable sleeve such that the biometric sensors may be positioned on the rollable sleeve to enable the rollable sleeve to be rolled.

The term "biometric sensor" or "sensor" generally refers to a component of a biometric measuring device that is configured to be placed in proximity with the skin of a limb or digit when the rollable sleeve is deployed on the limb or digit. A biometric sensor may be configured to respond to a stimulus (e.g., electrical, ultrasound, pressure, and/or light) and transmit a resulting output (as for measurement or operating a control). The term "in proximity with" is used herein to mean that a stimulus may be received by one or more of the biometric sensors from the skin of the subject without interference. Thus, a transparent structure (e.g., as a glass cover), intermediate substance (e.g., a transparent gel), or a small air gap may be interposed between the biometric measuring device and the skin of the subject.

The term "limb or digit" is used herein to refer to a finger, any portion of an arm (e.g., wrist, forearm, elbow), any portion of a leg (e.g., foot, ankle, calf, knee) or other body part suitable for taking biometric measurements.

The term "attached" is used herein to refer to a component of a biometric measuring device being embedded, received, woven, stitched, moulded, glued, connected, coupled, or any combination thereof.

Various embodiments are disclosed herein of a biometric measuring device for obtaining biometric measurements on a limb or digit, such as a finger. In various embodiments, the biometric measuring device may include a rollable sleeve that is rollable along a longitudinal axis of the limb or digit and multiple biometric sensors attached to the rollable sleeve such that the biometric sensors are positioned on the rollable sleeve to enable the sleeve to be rolled. In some embodiments, the biometric sensors are positioned to further enable the biometric sensors to be in proximity with the limb or digit when the rollable sleeve is rolled out (or deployed) over the longitudinal axis of the limb or digit. In some embodiments, the biometric sensors are positioned to further enable biometric information to be captured regardless of orientation of the rollable sleeve on the limb or digit. In various embodiments, the biometric sensors may include an optical sensor, an ultrasonic sensor, and a bio-impedance sensor, or any combination thereof.

In some embodiments, the biometric measuring device may include a fingerprint sensor attached to the rollable sleeve at a location that enables fingerprint data of the subject to be captured when the rollable sleeve is rolled out on a digit. In some embodiments, the biometric measuring device may include a processor coupled to the fingerprint sensor and the processor may be configured to verify the identity of the subject based on the fingerprint data captured by the fingerprint sensor and associate the obtained biometric measurements with the identity of the subject.

In some embodiments, the biometric measuring device may include one or more pressure sensors attached to the rollable sleeve in which the pressure sensors may be configured to determine a counter pressure applied to the limb or digit by the rollable sleeve. In some embodiments, the one or more pressure sensors may include a capacitive material strip, a piezo resistive film, and/or a strain gauge.

A biometric measuring device of the various embodiments may enable the application of several types of biometric sensor techniques to a subject's limb or digit using an integrated compact device. In some embodiments, the biometric measuring device may be used for verifying the identity of the patient and/or for verifying liveness, i.e., verifying that the finger is not a fake or spoof finger, and simultaneously. In some embodiments, the biometric measuring device may be configured for ambulatory monitoring during a patient's daily activities, including sporting activities, swimming, and/or showering. In some embodiments, the biometric measuring device may be configured to track counter pressure information useful for calibration of various biometric measurement techniques.

Figure 1B:
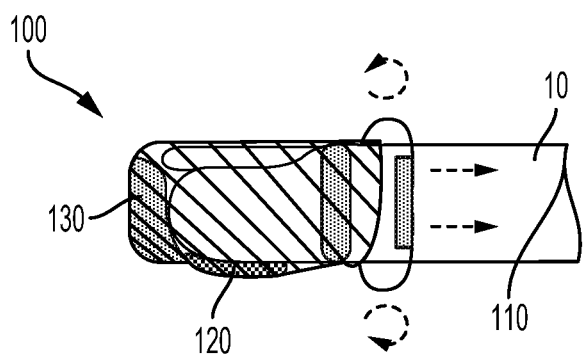
Figure 1C:
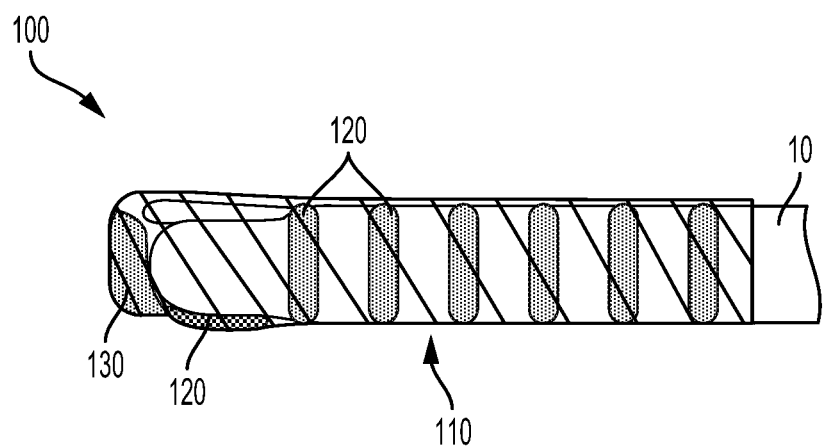

FIGS. 1A, 1B, and 1C illustrate a biometric measuring device 100 for obtaining various biometric measurements according to some embodiments. In the illustrated embodiment, the biometric measuring device 100 includes a rollable sleeve 110 that is rollable along a longitudinal axis 5 of a finger 10 or other limb. For example, a rollable sleeve 110 may include a sock, a wrist guard, an elbow brace, knee brace, or a calf sleeve. Multiple biometric sensors 120 may be attached to the rollable sleeve 110 for the purpose of obtaining the various biometric measurements. In some embodiments, the biometric measuring device 100 may include an auxiliary electronics package 130 that houses various electronic components for providing power, controlling sensor operation, processing sensor outputs, and/or communicating raw sensor or processed sensor outputs to remote computing devices for display or further processing.

FIG. 1A illustrates how at least a portion of the rollable sleeve 110 may be at least partially rolled up defining an annular opening 110a. In some embodiments, the rollable sleeve 110 may be partially rolled up, giving the biometric measuring device 100 a thimble-like appearance in a pre-deployed state ready for placement on the finger 10. As illustrated in FIG. 1B, a patient's finger 10 may be inserted into the annular opening 110a of the rollable sleeve 110. In some embodiments, the auxiliary electronics package 130 may be arranged at a closed end of the rollable sleeve 110 such that the auxiliary electronics package 130 abuts the patient's fingertip when inserted. Once the patient's finger is inserted, the rollable sleeve 110 may be rolled out over the rest of the finger 10 along the longitudinal axis 5 towards a fully extended state. When fully rolled out, the rollable sleeve 110 may extend from the patient's fingertip over one or more of the knuckles of the finger 10 as illustrated in FIG. 1C, for example.

In some embodiments, the rollable sleeve 110 may be manufactured from an elastic material. In some embodiments, the elastic material of the rollable sleeve 110 may be selected to have sufficient flexibility in the radial direction to implement the rollable sleeve 110 as "one size fits all." In some embodiments, the elastic material may be selected such that, when stretched over a limb, the material exerts a constant or variable counter pressure against the limb sufficient to maintain consistent contact with a skin surface and to limit movement between the sensors 120 and the skin surface. Non-limiting examples of an elastic material that may be used in the rollable sleeve 110 may include rubber, silicone, polydimethylsiloxane (PDMS), polytetrafluoroethylene (PTFE) e.g., Teflon™, or other elastic polymeric material.

In some embodiments, the rollable sleeve 110 may be fabricated from one or more layers of materials. For example, in some embodiments, the rollable sleeve 110 may include an elastic material layer interposed between two outer layers of non-woven materials. A non-woven material may be any fabric-like material made from long fibers, bonded together by chemical, mechanical, heat or solvent treatment. In some embodiments, the rollable sleeve 110 may be manufactured in the form of a woven fabric.

In some embodiments, the rollable sleeve 110 may be manufactured through a moulding process that involves creating a die in the shape of the limb (e.g., a finger), deploying the different sensors 120 along the die in a desired pattern, and then spraying or applying an elastic material (e.g., rubber or silicone) over the die and sensors in a desired flexible thickness.

In some embodiments, the rollable sleeve 110 may be configured with two open ends. In other embodiments, the rollable sleeve 110 may be configured with one open end and one closed end. The closed end may be sealed or provided with a cap to form the closed end.

In some embodiments, the rollable sleeve 110 may be configured to be rollable by positioning the biometric sensors 120 on the rollable sleeve 110 such that the sleeve may be rolled. In some embodiments, the rollable sleeve 110 may be configured to be rollable by using flexible (or at least partially flexible) materials and/or structures to implement the biometric sensors 120. In some embodiments, the biometric sensors 120 may be positioned to further enable biometric information to be captured regardless of orientation of the rollable sleeve on the limb or digit.

Figure 2:
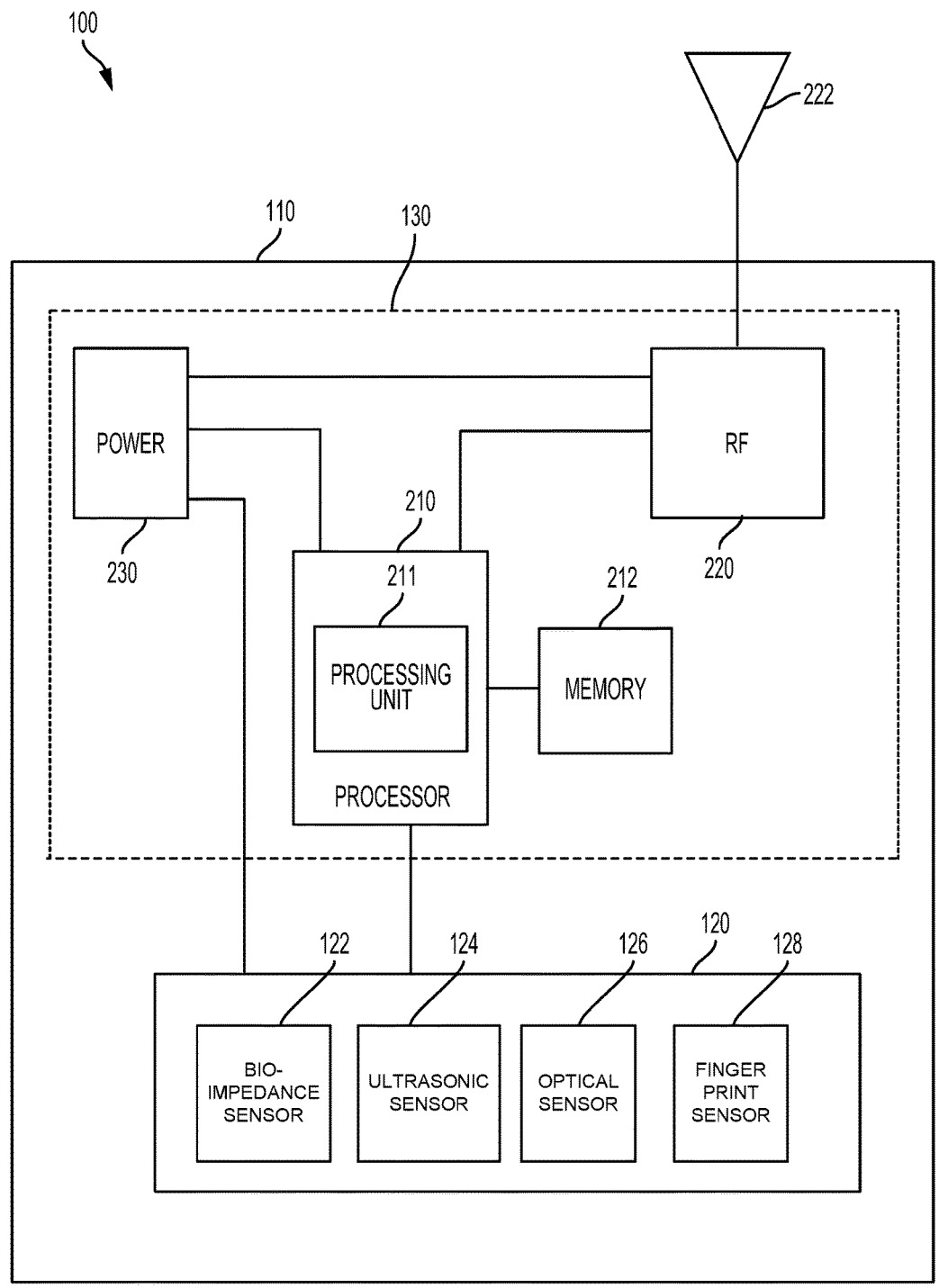
FIG. 2 illustrates components of a biometric measuring device according to some embodiments.

FIG. 2 illustrates components of a biometric measuring device 100 according to some embodiments. A biometric measuring device 100 may include multiple biometric sensors 120, a processor 210, memory 212, a radio frequency (RF) processor 220 coupled to an antenna 222, and a power supply 230. In various embodiments, some or all of the components of the biometric measuring device (e.g., 120, 210, 212, 220, 222, 230) may be attached along the length of a rollable sleeve 110.

Different types of biometric sensors may be attached to the rollable sleeve 110. In some embodiments, the multiple biometric sensors 120 may include a bio-impedance sensor 122, an ultrasonic sensor 124, an optical sensor 126, or any combination thereof, that may capture information from which biometric measurements may be obtained or calculated.

In some embodiments in which the rollable sleeve 110 is worn on a finger, the biometric sensors 120 may also include a fingerprint sensor 128 to capture information indicative of a patient's fingerprint and to associate the fingerprint data with outputs of one or more of the other biometric sensors 120 for identification or authentication purposes. In some embodiments, the finger print sensor 128 may be or include a Qualcomm Snapdragon Sense™ ID fingerprint sensor, which uses ultrasound to create three dimensional (3D) images of the features of a user's fingerprint. In some embodiments, the finger print sensor 128 may be configured to obtain pulse waveforms of an artery below the fingertip that may be used to provide multi-factor authentication in addition to the user's fingerprint data. In some embodiments, the finger print sensor 128 may be incorporated in a personal mobile device that obtains the user's fingerprint, e.g., instead of or in addition to the rollable sleeve 110. The user's fingerprint data may be used by a processor 210 for verifying the patient's identity.

Each of the biometric sensors 120 may be coupled to the processor 210 so that the processor receives the output of the sensors 120. In some embodiments, the processor 210 may be dedicated hardware specifically adapted to perform a variety of functions for the biometric measuring device 100.

In some embodiments, the processor 210 may be or include a programmable processing unit 211 that may be programmed with processor-executable instructions. In some embodiments, the processor 210 may be a programmable microprocessor, microcomputer or multiple processor chip or chips that can be configured by software instructions to perform a variety of functions of the biometric measuring device 100. In some embodiments, the processor 210 may be a combination of dedicated hardware and a programmable processing unit 211.

In some embodiments, the memory 212 may store processor-executable instructions and/or outputs from the biometric sensors 120. In some embodiments, the memory 212 may be volatile memory, non-volatile memory (e.g., flash memory), or a combination thereof. In some embodiments, the memory 212 may include internal memory included in the processor 210, memory external to the processor 210, or a combination thereof.

In some embodiments, the processor 210 may be configured to selectively control when the one or more biometric sensors 120 are activated (e.g., turned on and off). In some embodiments, the processor 210 may independently control the bio-impedance sensor 122, the ultrasonic sensor 124, the optical sensor 126, and the fingerprint sensor 128. For example, in some embodiments, the processor 210 may control activation of the bio-impedance sensor 122, the ultrasonic sensor 124, the optical sensor 126, and the fingerprint sensor 128, such that there may be a time delay between when the respective sensors are activated.

In some embodiments, the processor 210 may be configured to receive output signals from the respective sensors 120 and to calculate various biometric measurements, including cardiovascular properties inferred from the sensor output signals, for example. The processor 210 may also process output signals from the fingerprint sensor 128 in order to verify the identity of a subject based on the fingerprint data captured by the fingerprint sensor 128, and/or to associate the obtained biometric measurement with the verified identity.

In some embodiments, the processor 210 may be coupled to RF processor 220 coupled to an antenna 222 in order to communicate sensor output and/or measured biometric measurements via the antenna 222 to a remote computing device (not shown) for presentation through a display or other output device. The RF processor 220 may be a transmit-only or a two-way transceiver processor. For example, the RF processor 220 may include a single transceiver chip or a combination of multiple transceiver chips for transmitting and/or receiving signals. The RF processor 220 may operate in one or more of a number of radio frequency bands depending on the supported type of communications.

The processor 210 may be configured to transmit measured or calculated biometric measurement information, including measured values of the cardiovascular properties or the output from the biometric sensors 120, to a remote computing device (not shown) for recording or display. Such a remote computing device may be any of a variety of computing devices, including but not limited to a processor in smart clothing, cellular telephones, smart-phones, web-pads, tablet computers, Internet enabled cellular telephones, wireless local area network (WLAN) enabled electronic devices, laptop computers, dedicated healthcare electronic devices, personal computers, and similar electronic devices equipped with at least a processor and a communication resource to communicate with the RF processor 220. Measured and/or calculated biometric measurement information may be transmitted from the biometric measuring device 100 to a remote computing device over a wireless link using Bluetooth®, Wi-Fi® or other wireless communication protocol.

The biometric sensors 120, the processor 210, the RF processor 220, and any other electronic components of the biometric measuring device 100 may be powered by a power supply 230. The power supply 230 may be a battery, a solar cell or other energy harvesting power supply.

In some embodiments, the processor 210, the RF processor 220, the power supply 230 and other electronic components may be housed in a compact auxiliary electronics package 130. In some embodiments, the auxiliary electronics package 130 may be inserted into a closed distal end of the biometric measuring device 100. In some embodiments, the auxiliary electronics package 130 may be connected by a electrical connections 315, such as a cable, enabling the auxiliary electronics package 130 to be positioned remote from the biometric measuring device 100. For example, the electronic components may be integrated into an application specific integrated circuit (ASIC) or configured as discrete components mounted on an embedded flexible electronic or circuit board that may be placed at the fingertip. In some embodiments, the processor 210, the RF processor 220, the power supply 230 and other electronic components may be distributed along a length of the rollable sleeve 110 along with the biometric sensors 120.

Figure 3A:
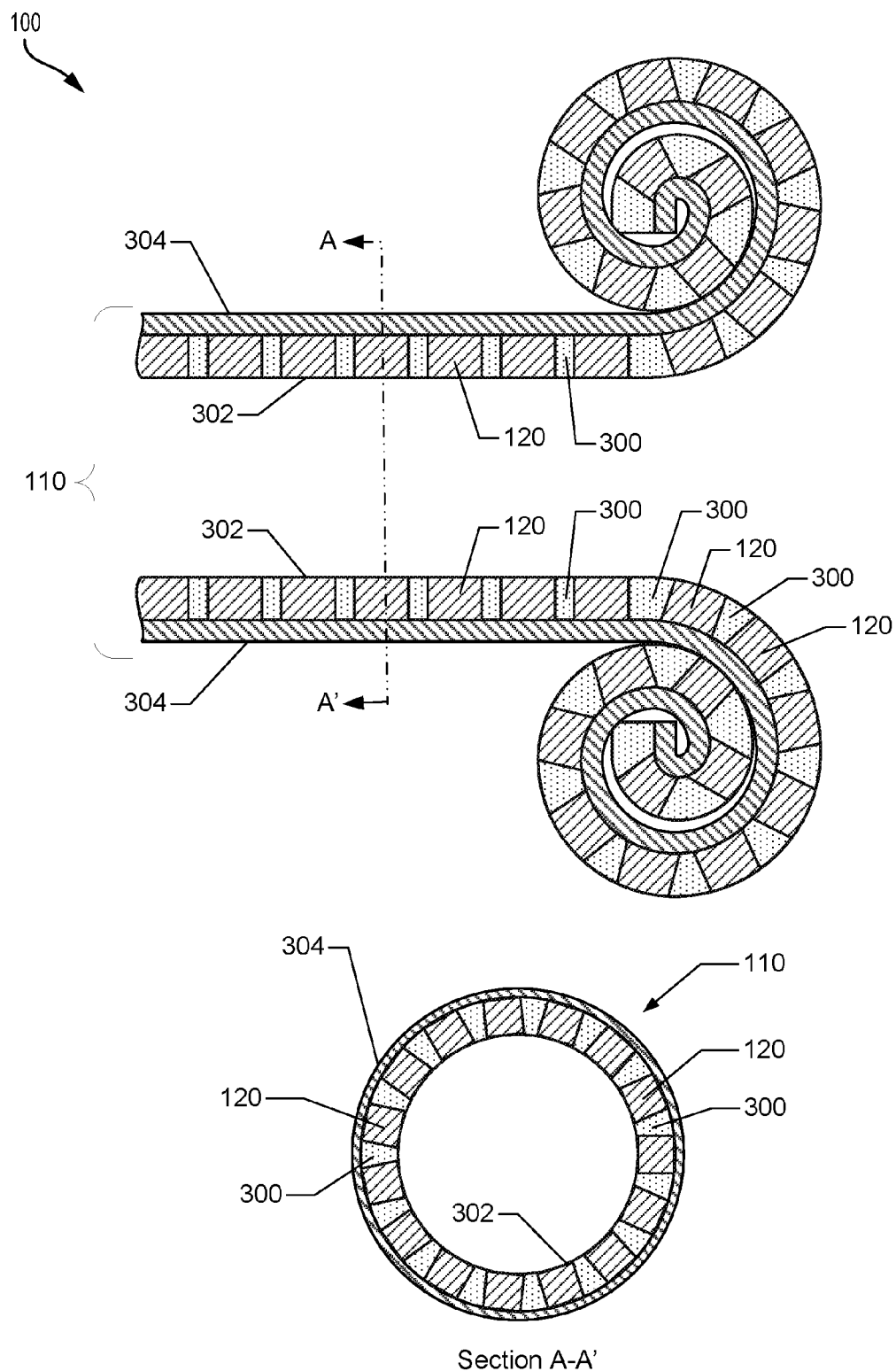
FIG. 3A illustrates cross-section and front elevation views of a biometric measuring device configured to be rollable based on the positions of the biometric sensors according to some embodiments.

FIG. 3A illustrates cross-section views of a biometric measuring device 100 configured to be rollable based on the positions of the biometric sensors 120 according to some embodiments. For example, the rollable sleeve 110 may be configured to be rollable based on the positions of the biometric sensors regardless of whether the biometric sensors 120 include structural components that are not amenable to bending or flexing.

In some embodiments, the biometric sensors 120 may be positioned, such that the biometric sensors may be arranged in rows defined along the length of the sleeve. Each row of biometric sensors 120 may be offset from adjacent rows of biometric sensors 120 by gaps (collectively or individually 300) of sufficient size that enables the sleeve 110 to be rolled. In some embodiments, the gaps 300 may be positioned between biometric sensors 120 radially as illustrated in section view A-A'. In some embodiments, each row of biometric sensors 120 may form an annular (or partially annular) region or ring of sensors that extends around the circumference (or partial circumference) of the sleeve 110.

In some embodiments, the biometric sensors 120 may be positioned such that the biometric sensors are arranged in rows and columns defined along the length of the sleeve, collectively forming a two-dimensional (2D) matrix of sensors as illustrated in FIG. 3A. Each row and column of biometric sensors 120 may be offset laterally and longitudinally from adjacent rows and columns of sensors by gaps 300 of sufficient size that enables the sleeve 110 to be rolled.

In some embodiments, the gaps 300 may include the material or fabric of the rollable sleeve 110. In some embodiment, the gaps 300 may include air gaps or other compressible dividers in the rollable sleeve 110. In some embodiments, the biometric sensors 120 and gaps 300 may be interposed between an inner surface layer 302 and a backing layer 304 of the rollable sleeve 110. In some embodiments, the biometric sensors 120 may be attached to the inner surface layer 302 of the rollable sleeve 110.

Figure 3B:
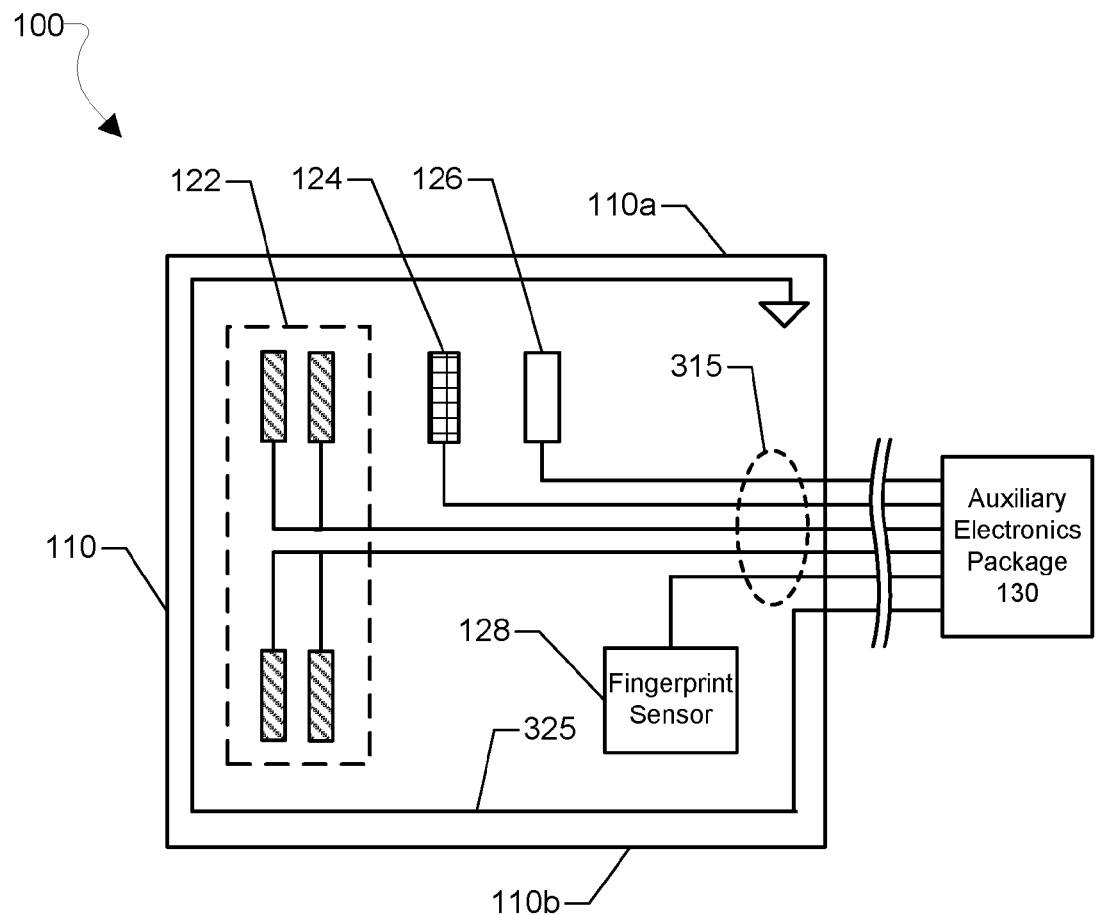
FIG. 3B illustrates a biometric measuring device manufactured with different types of biometric sensors according to some embodiments.

FIG. 3B illustrates a biometric measuring device 100 manufactured with different types of biometric sensors according to some embodiments. As illustrated, the biometric measuring device 100 may include a bio-impedance sensor 122, an ultrasonic sensor 124, an optical sensor 126, and a finger print sensor 128 attached to the rollable sleeve 110 (shown cut open along a longitudinal axis). In some embodiments, the longitudinal edges 110*a* and 110*b* of the rollable sleeve 110 may be sealed or woven together, such that the bio-impedance sensor 122, the ultrasonic sensor 124, the optical sensor 126, the finger print sensor 128, or any combination thereof, are disposed on the inner surface layer (e.g., 302) of the rollable sleeve 110.

In some embodiments, the biometric sensors (e.g., 122, 124, 126, 128) may be printed on the elastic or non-woven material of the rollable sleeve 110 using conductive inks. Printing may be performed using various techniques, including but not limited to screen printing, inkjet printing, and roll-to-roll processing. In some embodiments, the biometric sensors may be configured as flexible (or at least partially flexible) monolithic planar devices capable of being manufactured directly on, woven into or otherwise attached to the rollable sleeve 110. In embodiments in which the biometric sensors 120 are integrated into woven fabrics or materials, the biometric sensors may be supported on narrow strips of flexible circuit boards that may be attached to the woven fabric or material. In some embodiments, the biometric sensors may include rigid or at least partially rigid structural components.

Electrical connections 315 between the biometric sensors 122, 124, 126, and 128 and the electronic components of an auxiliary electronics package 130 may employ flexible (or at least partially flexible) conductors or cables to enable the rollable sleeve 110 to be rolled out over a limb or digit (e.g., finger). For example, in some embodiments, the electrical connections 315 may be implemented as conductive ink traces printed directly on the rollable sleeve 110 between each of the biometric sensors 122, 124, 126, 128 and the auxiliary electronics package 130.

In some embodiments, the conductive ink traces may be printed on the rollable sleeve 110 in a helical pattern in order to allow the electrical connections 315 to stretch without breaking. In some embodiments in which the elastic material of the rollable sleeve 110 is stretchable in one direction (e.g., radial direction of the finger), the conductive ink traces may be aligned perpendicular to that direction in order to allow the electrical connections 315 to stretch without breaking. In some embodiments, the electrical connections 315 may be or include insulated wires. For example, in embodiments in which the rollable sleeve 110 is fabricated using or including a woven fabric, the wires may be woven into the fabric and connected between the biometric sensors 122, 124, 126, 128 and the electronic components of an auxiliary electronics package 130.

In some embodiments, an electrical wire or trace 325 may be configured in the form of a Faraday cage attached to the rollable sleeve 110 in order to electrically shield the bio-impedance sensor 122, the ultrasonic sensor 124, the optical sensor 126, the finger print sensor 128, or any combination thereof. In some embodiments, the electrical wire or trace 325 may serve as an antenna in order to communicate the calculated measurements of various biometric properties and/or the output data from the sensors to a remote computing device (e.g., antenna 222 of FIG. 2).

In some embodiments, the biometric sensors 120 may be positioned to further enable biometric information to be captured regardless of orientation of the rollable sleeve on the limb or digit. For example, a particular type of biometric sensor 120 (e.g., bio-impedance, optical or ultrasonic) may be attached to the rollable sleeve 110 at multiple different locations and/or orientations about a central axis. In some embodiments, a particular type of biometric sensor may be attached to the rollable sleeve 110 multiple times to form a specific pattern of sensors, such as a helical pattern for example. By attaching multiple sensors of the same type in a particular pattern, the processor (e.g., 210) may be configured to search for and identify one or more sensors capable of providing an output signal from which to obtain the desired biometric measurements. In some embodiments, the processor may be configured to activate and test the output signals from each of the sensors 120 simultaneously, one at time, or in various groupings to identify the one or more sensors capable of providing the desired or required measurements.

Figure 4A:
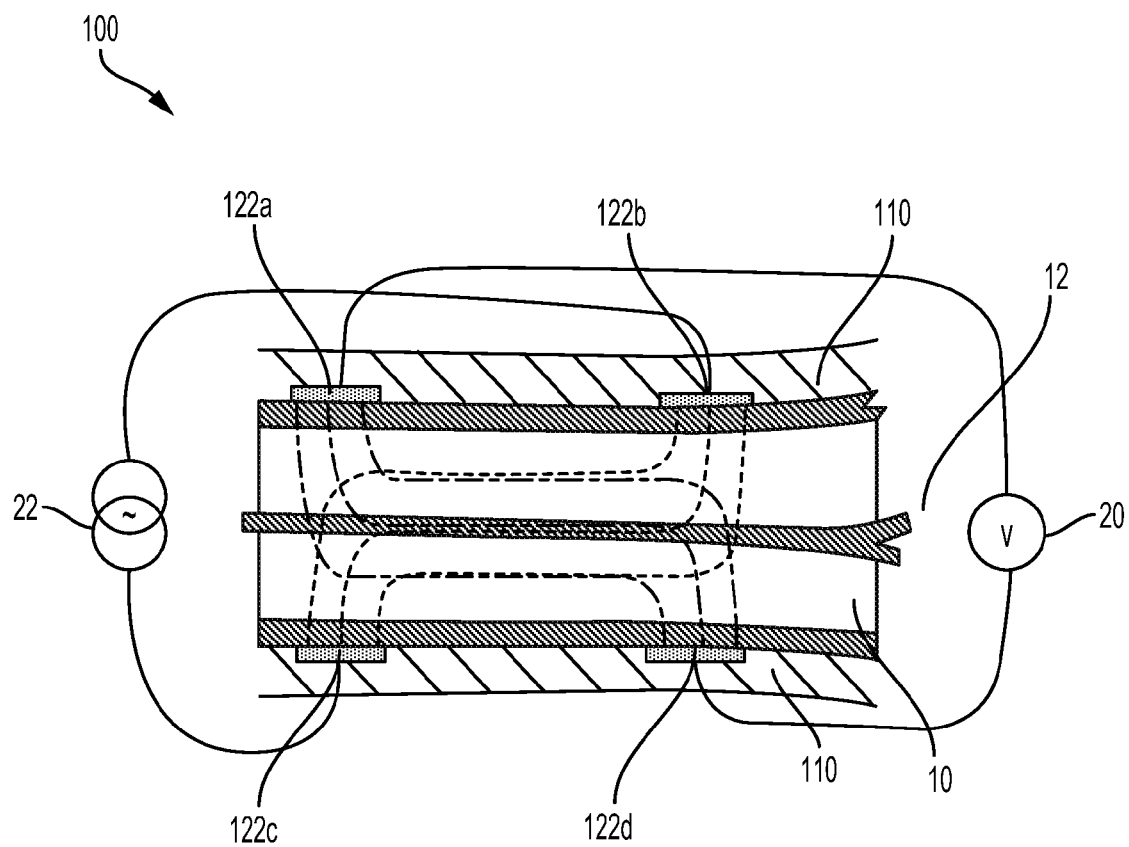
FIG. 4A illustrates a bio-impedance sensor operating on a portion of the biometric measuring device according to some embodiments.

FIG. 4A illustrates a bio-impedance sensor 122 operating on a portion of the biometric measuring device 100 according to some embodiments. As illustrated, the bio-impedance sensor 122 of FIG. 3 may be implemented with four planar electrodes 122*a*, 122*b*, 122*c*, and 122*d* (collectively, electrodes 122) arranged along an interior surface of the rollable sleeve 110. In some embodiments, a conductive gel or adhesive may be applied to a surface of the electrodes in order to facilitate the electrical contact between the electrodes 122 and the skin.

In operation, a voltage 20 may be applied by a processor (e.g., processor 210 of FIG. 2) or an impedance sensor across one pair of electrodes 122*a*, 122*d* to generate an electric field across an artery 12 of the finger 10. In some embodiments, a voltage 20 with a high excitation frequency may facilitate sufficient capacitive coupling into the skin. Current or voltage sensed 22 across the other pair of electrodes 122*b*, 122*c* may be used by the processor or impedance sensor to detect changes in bio-impedance from which various cardiovascular properties may be inferred based on detected time-varying bio-impedance values, such as heart rate and arterial distension for example.

In some embodiments, more or fewer electrodes 122 may be used to implement the bio-impedance sensor. In some embodiments, a second bio-impedance sensor may be integrated within the rollable sleeve 110 at a location spaced apart from a first bio-impedance sensor. By coupling the outputs from the two bio-impedance sensors to the processor 210, the processor 210 may be configured to measure cardiovascular properties that may require output from at least two sensor locations, such as pulse transit time (PTT) and pulse wave velocity.

Figure 4B:
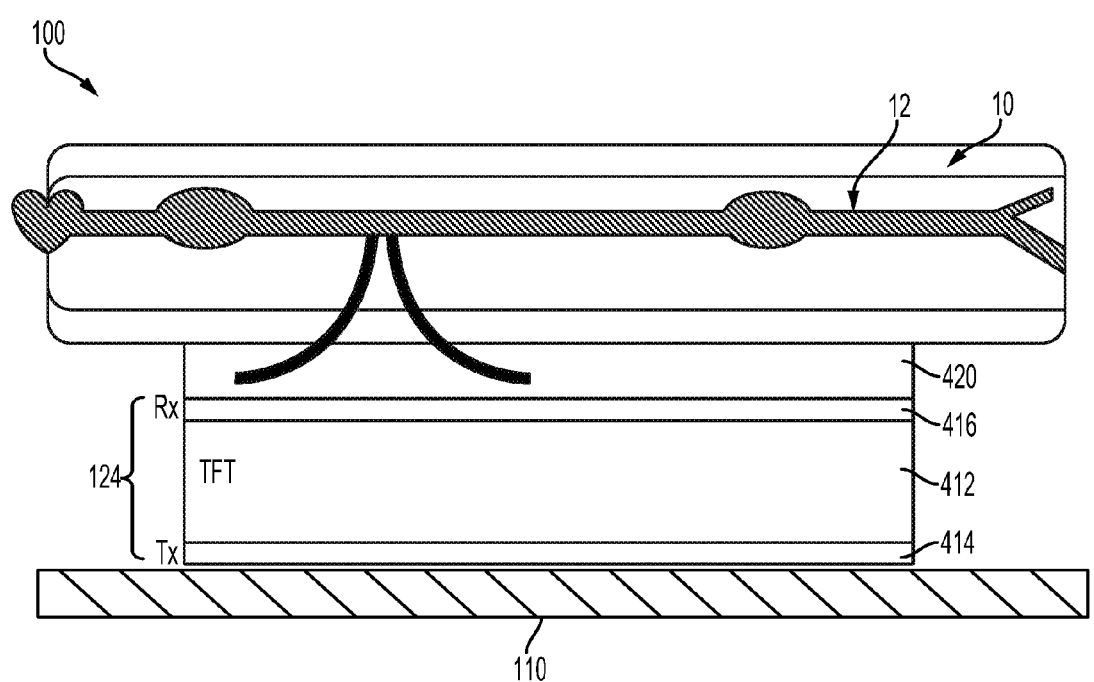
FIG. 4B illustrates an ultrasonic sensor operating on a portion of the biometric measuring device according to some embodiments.

FIG. 4B illustrates an ultrasonic sensor 124 operating on a portion of the biometric measuring device 100 according to some embodiments. As illustrated, the ultrasonic sensor 124 may be implemented as a flexible (or at least partially-flexible), planar, multi-layer, monolithic ultrasonic transducer. The planar ultrasonic transducer may include a thin film transistor (TFT) layer 412 interposed between two piezoelectric film layers 414, 416. In some embodiments, the piezoelectric film layers may each include a flexible, polarized, polyvinylidene fluoride (PDVF) film. In some embodiments, an acoustic matching layer 420 may be deployed on the surface of the ultrasonic sensor 124 in order to improve the acoustic coupling between the transducer and the skin and tissue of a limb, such as a finger 10. In some embodiments, the acoustic matching layer 420 may be provided as a solid acoustic gel.

In response to an alternating current (AC) voltage being applied to the transmit piezoelectric film layer 414, ultrasonic waves may be emitted from the transmit piezoelectric film layer 414 towards the finger 10. The AC voltage may be coupled to the transmit piezoelectric film layer 414 through electrical connections (e.g., 315 of FIG. 3) from a processor (e.g., 210 of FIG. 2).

As the ultrasonic waves propagate through the finger 10, the ultrasonic waves are reflected by the artery 12 and the surrounding tissues. In some embodiments, the reflected waves 20 may be sensed by the receive piezoelectric film layer 416, which converts the reflected waves 20 into electrical signals (e.g., current or voltage signals). Columns and rows of individual amplifiers (not shown) may be embedded in the TFT layer 412 to detect and amplify the electrical signals. The electrical signals may be output from the TFT layer 412 and coupled through electrical connections (e.g., 315 of FIG. 3) to an input of a processor (e.g., 210 of FIG. 2) for processing. For example, the processor may process the electrical output signals received from the TFT layer 412 in order to generate time varying distance measurements or images of the artery and surrounding tissues from which various cardiovascular properties may be calculated or inferred.

In some embodiments, the ultrasonic sensor 124 may be implemented in several strips aligned in parallel such that each strip of the planar ultrasonic transducer corresponds to a row or column of TFT amplifiers. By segmenting the planar ultrasonic transducer into strips, the strips may be woven into a woven fabric or material of the rollable sleeve 110. If several strips are aligned in parallel, then a matrix of ultrasound transducers may be established that may be controlled in order to enable ultrasound beam steering of both transmitted ultrasound and received reflected sound. In some embodiments, each strip of the planar ultrasonic transducer may be implemented on flexible circuit board (not shown) that may be woven into the woven fabric or material.

In some embodiments, a second ultrasonic sensor may be integrated within the rollable sleeve 110 at a location spaced apart from a first ultrasonic sensor. By coupling the outputs from the two ultrasonic sensors to the processor 210, the processor 210 may be configured to measure cardiovascular properties that require information gathered from at least two sensor locations, such as pulse transit time (PTT) and pulse wave velocity.

Figure 4C:
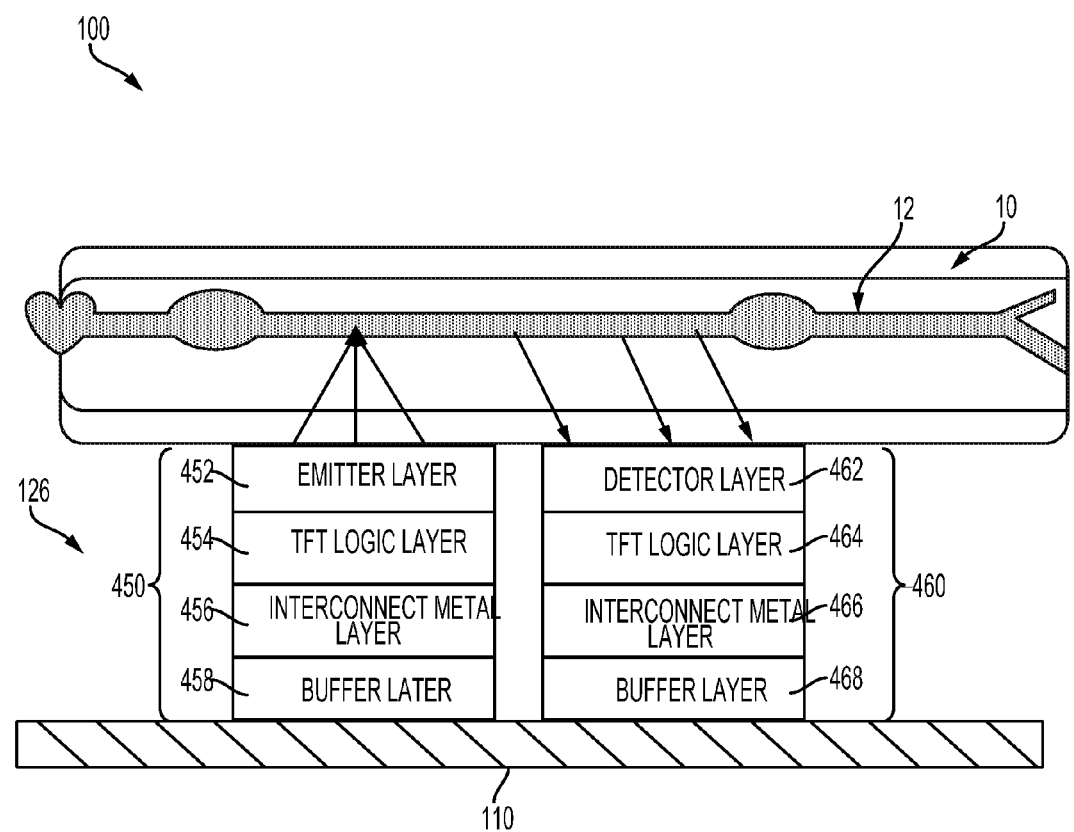
FIG. 4C illustrates an optical sensor implemented within a portion of the biometric measuring device according to some embodiments.

FIG. 4C illustrates an optical sensor 126 implemented within a portion of the biometric measuring device 100 according to some embodiments. As illustrated, the optical sensor 126 may be implemented as a flexible (or at least partially flexible), planar, multi-layer, monolithic optical transducer arranged on a surface of the rollable sleeve 110.

In some embodiments, the planar optical transducer may include an organic light emitting diode (OLED) cell (or a matrix of OLED cells) 450 and an organic photodiode (OPD) cell (or a matrix of OPD cells) 460. The OLED cell(s) 450 may emit light in the direction of an artery 12 in a limb, such as a finger 10. As the light propagates through the finger 10, some of the light is reflected by the artery 12 and the surrounding tissues of the finger 10. In some embodiments, the reflected light may be detected by the OPD cell(s) 460, which may convert the reflected light into electrical signals (e.g., current or voltage signals). The electrical signals may be output from the OPD cell(s) 460 and coupled through electrical connections (e.g., 315 of FIG. 3) to an input of a processor (e.g., 210 of FIG. 2) for processing. For example, the processor may process the electrical output signals received from the OPD cell(s) 460 in order to calculate or infer various cardiovascular properties.

In some embodiments, the OLED cell(s) 450 and OPD cell(s) 460 may include several layers manufactured directly on the rollable sleeve 110. For example, in some embodiments, an OLED cell 450 may include an emitter layer 452, a thin film transistor (TFT) logic layer 454, an interconnect metal layer 456, and a buffer layer 458. In some embodiments, an OPD cell 460 may include a detector layer 462, a thin film transistor (TFT) logic layer 464, an interconnect metal layer 466, and a buffer layer 468.

In some embodiments, where the optical sensor 124 may be integrated into woven fabrics or materials, the OLED cell(s) 450 and the OPD cells 460 may be manufactured on narrow strips of flexible circuit boards that may be stitched, woven, glued, or otherwise attached to the woven fabric or material. In some embodiments, each flexible circuit board may support at least one pair of OLED and OPD cells. In some embodiments, some of the flexible circuit boards may support only OLED cells, while some of the other flexible circuit boards support only OPD cells.

In some embodiments, a second planar optical transducer may be attached to the rollable sleeve 110 at a location spaced apart from a first planar optical transducer. By coupling the outputs from the two planar optical transducers to the processor (e.g., 210 of FIG. 2), the processor may be configured to measure cardiovascular properties that may require information gathered from at least two sensor locations, such as pulse transit time (PTT) and pulse wave velocity.

Figure 5:
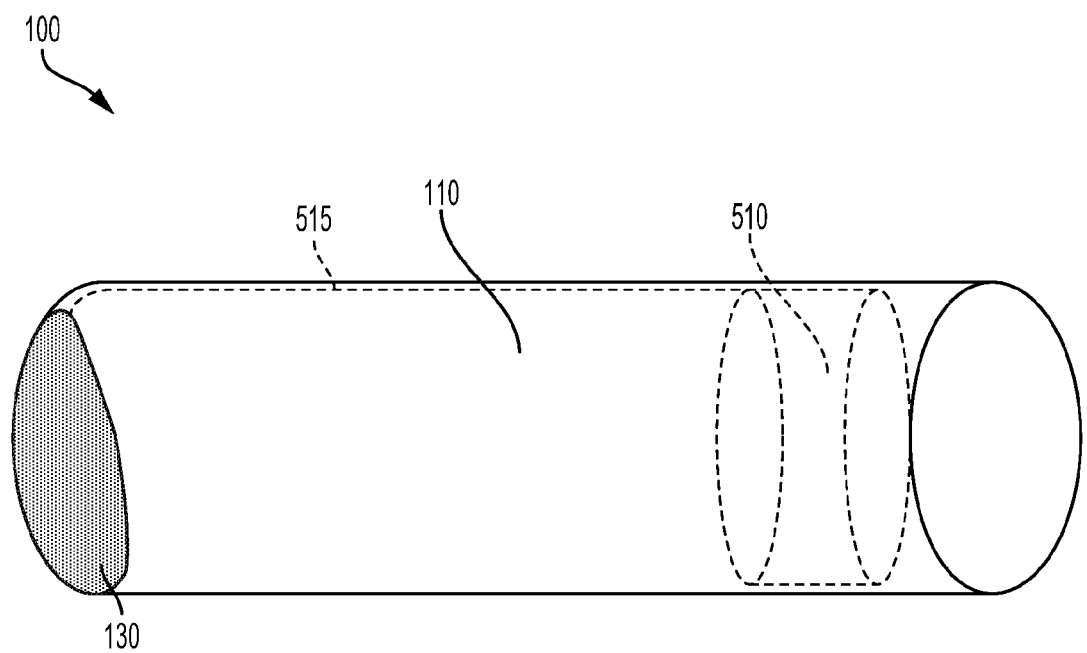
FIG. 5 illustrates a biometric measuring device configured to detect a counter pressure applied by the rollable sleeve to a limb according to some embodiments.

FIG. 5 illustrates a biometric measuring device 100 configured to detect a counter pressure applied by the rollable sleeve 110 to a limb according to some embodiments. For measurements of some cardiovascular properties (e.g., arterial distension and pulse transit time), any counter pressure applied by the biometric measuring device 100 may affect the artery and thus the cardiovascular measurements corresponding to that artery. Due to an artery's sensitivity to counter pressure, monitoring the counter pressure applied to a limb or finger by the rollable sleeve 110 may be useful in obtaining accurate biometric measurements.

In some embodiments, the elastic material of the rollable sleeve 110 may be selected to provide a constant counter pressure during bending of a limb, e.g., a finger, and due to different limb sizes. For example, the selected material may provide a constant contraction force against the limb independent of an expected amount of strain applied to the rollable sleeve 110. In some embodiments, the selected material may be a polymer associated with a flat Young's modulus versus strain such that the constant counter pressure is known.

In some embodiments, the counter pressure applied by the rollable sleeve 110 may be monitored by one or more pressure sensors 510. For example, the pressure sensor 510 may be a planar strain gauge attached to the sleeve. In other examples, the pressure sensor 510 may be a strip of a material attached to the sleeve having a property that changes according to a known linear or a polynomial relationship to the strain applied to the material.

Non-limiting examples of materials that may be used for the pressure sensor 510 include polyvinylidene fluoride (PVDF) peizo resistive films, which generates an output voltage proportional to the strain on the capacitive material. For example, as the rollable sleeve 110 stretches due to finger bending or finger size, a strip of PDVF peizo resistive film may generate a voltage that is proportional to the corresponding strain experienced by the PDVF strip. In some embodiments, the strain may correspond to the extension of the sleeve (e.g., in millimeters (mm)). The voltage signal may be coupled via a connector or trace 515 from the pressure sensor 510 to a processor (e.g., 210 of FIG. 2).

Other materials that may be used for implementing the pressure sensor 510 may include elastic capacitive films that, when stretched, exhibit a change in the capacitance measured across the film.

In some embodiments, the processor may determine the counter pressure applied by the rollable sleeve 110 from the change in voltage or capacitance of the pressure sensor 510. For example, by selecting a material for the pressure sensor 510 that has a known relationship between voltage or capacitance and strain, the processor may determine the amount of strain on the rollable sleeve 110 from the measured voltage or capacitance obtained from the pressure sensor 510. Further, because the stress-to-strain relationship (e.g., Young's modulus) of the capacitive material is typically known, the processor can determine the amount of stress (or counter pressure) that is applied by the rollable sleeve 110 from the strain corresponding to the change in voltage or capacitance of the pressure sensor 510.

Figure 6:
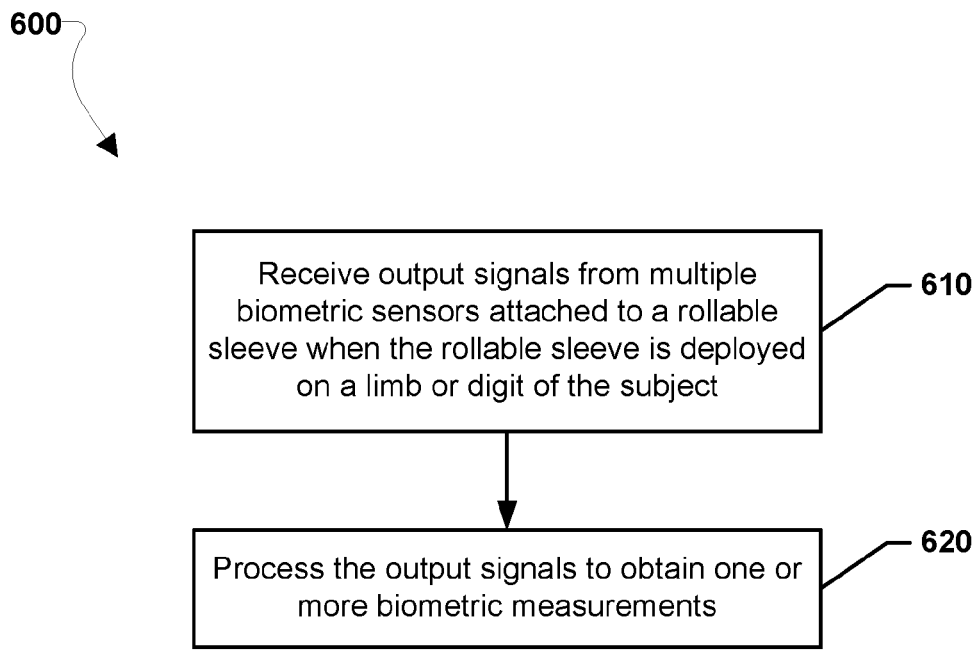
FIG. 6 illustrates a method for measuring a biometric property of a subject using a biometric measuring device according to some embodiments.

FIG. 6 illustrates a method 600 for measuring a biometric property of a subject using a biometric measuring device according to some embodiments. The method 600 may be implemented using any of the embodiments of a biometric measuring device described herein.

In block 610, the processor (e.g., 210 of FIG. 2) may receive output signals from multiple biometric sensors (e.g., 120) attached to the rollable sleeve when the rollable sleeve is deployed on a limb or digit of the subject. In some embodiments, the output signals may be received from each of the biometric sensors 120 via electrical connections (e.g., 315 of FIG. 3) in the form of wires or conductive ink traces. In some embodiments, the processor may receive output signals in response to the processor applying an electrical signal specifically adapted to activate each of the biometric sensors 120.

In block 620, the processor (e.g., 220 of FIG. 2) may optionally process the output signals from the respective biometric sensors 120 in order to obtain one or more biometric measurements, such as measurements of various cardiovascular properties. For example, in some embodiments, the generated output from the respective biometric sensors 120 may be in the form of a pulse waveform signal having both alternating current (AC) and direct current (DC) components. The AC signal component may correspond to the optical response of an artery of interest, while the DC signal component may correspond to the optical response of non-dynamic tissues that surround the artery. In order to obtain the AC signal component of the pulse waveform for the artery, the processor may process the pulse waveform signal through a high pass filter having a cut-off frequency in the order of 0.5 Hertz (Hz) or lower.

As part of the operations in block 620, the processor may use the output signal from the one or more biometric sensors 120 to calculate a variety of cardiovascular properties, such as arterial distension, pulse transit time (PTT), pulse wave velocity (PWV), mean arterial cross-sectional area, arterial stiffness, heart rate, heart rate variability, blood flow, blood oxygen levels ($SpO_2$), and blood pressure, as well as calibration procedures for one or more of such measurements. For example, in some embodiments, the processor may track changes in the AC signal component over time in order to determine one or more cardiovascular properties, including cross-sectional area and distension of an artery, for example.

In some embodiments, the processor may determine oxygen levels in the blood (SpO2) based on differences in the absorption of two different wavelengths of light obtained from the output of an optical sensor 122. For example, the blood oxygen level may be measured as a ratio between a mean of the measured DC and AC components for two wavelengths of light (e.g., one wavelength may be red (e.g., 660 nanometers (nm)) and the other wavelength may be infrared (e.g., on the order of 950 nm).

In some embodiments, the biometric measuring device 100 may include at least two biometric sensors 120 spaced apart in parallel to a longitudinal direction of the artery to measure certain cardiovascular properties, such as a pulse transit time (PTT). In such embodiments, in block 620 the processor may compute the pulse transit time (PTT) based on a time shift between the AC signal components of two pulse waveforms detected at the respective sensor locations. For example, the processor may determine the time shift by (i) correlating the systolic parts of the two pulse waveforms, (ii) finding the minimum just before the systolic onset of the two pulse waveforms, and then observing the time difference, (iii) finding the maximum and minimum of the two pulse waveforms, identifying a point on the slope corresponding to a given ratio of the wave forms, and determining the time shift between these two points, or (iv) detecting the zero crossing of the high pass filtered versions of the waveforms.

In some embodiments, in block 620 the processor may calculate the heart rate by estimating the time between pulses or by estimating characteristic periodicities in sequence of pulses based on the output received from the one or more biometric sensors 120.

In some embodiments, in block 620 the processor may calculate blood pressure based on the signal variation that is synchronous with the heartbeat. For example, blood pressure may be calculated by the processor in block 620 from various combinations of cardiovascular properties determined from the output received from the one or more biometric sensors 120. Such cardiovascular properties may include, but are not limited to, arterial distension, and arterial mean cross sectional area.

Figure 7:
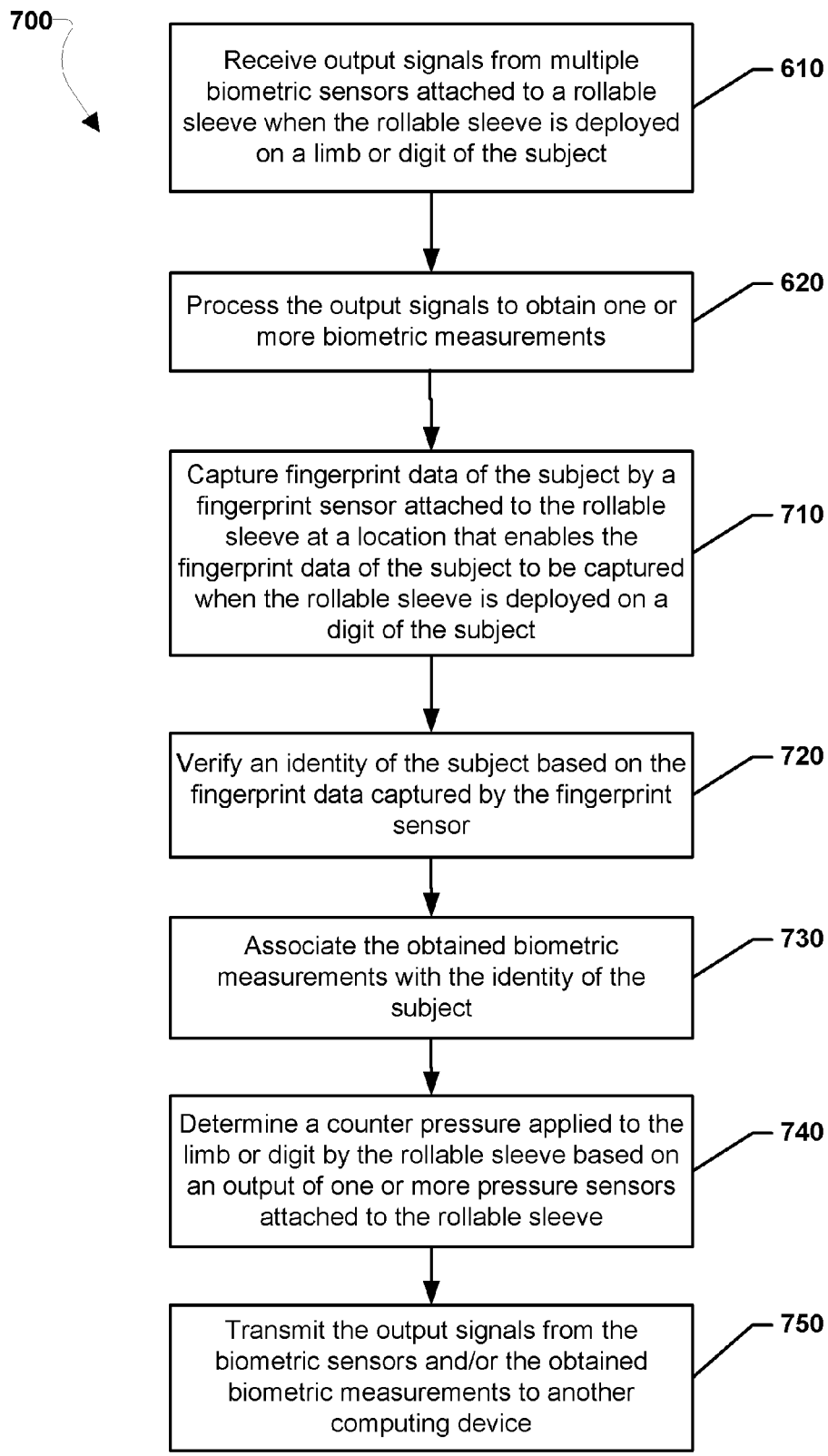
FIG. 7 illustrates another method of for measuring a biometric property of a subject using a biometric measuring device according to some embodiments.

FIG. 7 illustrates another method 700 of for measuring a biometric property of a subject using a biometric measuring device according to some embodiments. The method 700 may include operations in blocks 610 and 620 as described with reference to FIG. 6.

In block 710, a fingerprint sensor (e.g., 128 of FIG. 2) that is attached to the rollable sleeve (e.g., 110) may capture fingerprint data of the subject when the rollable sleeve is deployed on a digit (e.g., finger) of the subject. For example, in some embodiments, the finger print sensor 128 may be or include a Qualcomm Snapdragon Sense™ ID fingerprint sensor, which uses ultrasound to create three dimensional (3D) images of the features of a user's fingerprint. In some embodiments, the finger print sensor 128 may be configured to obtain pulse waveforms of an artery below the fingertip that may be used to provide multi-factor authentication in addition to the user's fingerprint data.

In block 720, the processor (e.g., 210 of FIG. 2) may verify the identity of the subject based on the fingerprint data captured by the fingerprint sensor (e.g., 128). For example, the processor may be configured to verify the identity of the subject by transmitting a verification request to a remote computing device. In some embodiments, the verification request may include the fingerprint data obtained by the fingerprint sensor (e.g., 128) to be compared by the remote computing device against reference fingerprint data for the subject maintained in a database accessible to the remote computing device. In response to transmission of the verification request, the processor (e.g., 210) may receive a verification signal from the remote computing device indicating whether or not the fingerprint data obtain by the fingerprint sensor matches the fingerprint data maintained of the reference data set for the subject. In some embodiments, the processor may receive an identifier for the subject when the fingerprint data is verified.

In block 730, the processor (e.g., 210 of FIG. 2) may associate the obtained biometric measurements with the identity of the subject. For example, in some embodiments, the processor may be configured to associate the obtained set of biometric measurements with the identifier obtained for the subject during verification at block 720. This may enable the biometric measurements to be subsequently transmitted or displayed in conjunction with the subject's identifier.

In block 740, the processor may determine a counter pressure applied to the limb or digit by the rollable sleeve based on an output of one or more pressure sensors (e.g., 510 of FIG. 5) attached to the rollable sleeve. In some embodiments, the processor may use the counter pressure as an input for processing the output signals to obtained the one or more biometric measurements from the output signals in block 620. For example, any counter pressure applied by the rollable sleeve 110 may affect the artery and thus the cardiovascular measurements corresponding to that artery. Due to an artery's sensitivity to counter pressure, monitoring the counter pressure applied to a limb or digit by the rollable sleeve 110 may be useful in obtaining accurate biometric measurements.

In block 750, the processor (e.g., 210) may transmit the output signals from the biometric sensors and/or the obtained measurement to another computing device, such as via an RF processor and an antenna (e.g., 220 and 222 of FIG. 2). For example, in some embodiments, the output signals received from the respective biometric sensors in block 620 may be transmitted directly to another computing device (e.g., a smartphone), such as via the RF processor 230. In such embodiments, the computing device may calculate cardiovascular properties from the output signals, enabling the use of a limited capability processor (e.g., the processor 210 of FIG. 2) in the biometric measuring device 100. In some other embodiments, the processor may transmit calculated cardiovascular property measurements to a mobile device, such as a smart phone, via a wireless signal, such as Bluetooth or Wi-Fi, for display to an operator. The computing device may store, process, and/or display calculated cardiovascular property measurements.

Those of skill in the art will appreciate that the foregoing method description and the process flow diagram are provided merely as illustrative examples and are not intended to require or imply that the operations of the various embodiments must be performed in the order presented. The operations in the foregoing embodiment methods may be performed in any order. Further, any reference to claim elements in the singular, for example, using the articles "a," "an" or "the" is not to be construed as limiting the element to the singular.

The various illustrative logical blocks, circuits, and algorithm operations described in connection with the embodiments disclosed herein may be implemented as electronic hardware, computer software, or combinations of both. To clearly illustrate this interchangeability of hardware and software, various illustrative components, blocks, circuits, and operations have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the claims.

The hardware used to implement the various illustrative logics, logical blocks, and circuits described in connection with the embodiments disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor may be a microprocessor, but, in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration. Alternatively, some operations or methods may be performed by circuitry that is specific to a given function.

The functions in the various embodiments may be implemented in hardware, software, firmware, or any combination thereof. If implemented in software, the functions may be stored as one or more processor executable instructions or code on a non-transitory computer readable medium or non-transitory processor readable medium. The operations of a method or algorithm disclosed herein may be embodied in processor-executable software that may be stored on a non-transitory computer-readable or processor-readable storage medium. Non-transitory computer-readable or processor-readable storage media may be any storage media that may be accessed by a computer or a processor. By way of example but not limitation, such non-transitory computer-readable or processor-readable media may include RAM, ROM, EEPROM, FLASH memory, CD-ROM or other optical disk storage, magnetic disk storage or other magnetic storage devices, or any other medium that may be used to store desired program code in the form of instructions or data structures and that may be accessed by a computer. Disk and disc, as used herein, includes compact disc (CD), laser disc, optical disc, digital versatile disc (DVD), floppy disk, and Blu-ray disc where disks usually reproduce data magnetically, while discs reproduce data optically with lasers. Combinations of the above are also included within the scope of non-transitory computer-readable and processor-readable media. Additionally, the operations of a method or algorithm may reside as one or any combination or set of codes and/or instructions on a non-transitory processor-readable medium and/or computer-readable medium, which may be incorporated into a computer program product.

The preceding description of the disclosed embodiments is provided to enable any person skilled in the art to make or use the claims. Various modifications to these embodiments will be readily apparent to those skilled in the art, and the generic principles defined herein may be applied to other embodiments without departing from the scope of the claims. Thus, the claims are not intended to be limited to the embodiments shown herein but are to be accorded the widest scope consistent with the following claims and the principles and novel features disclosed herein.

What is claimed is:

1. A biometric measuring device for obtaining biometric measurements on a limb or digit of a subject, comprising:
a rollable sleeve, wherein the rollable sleeve is rollable along a longitudinal axis of the limb or digit; and a plurality of biometric sensors attached to the rollable sleeve, wherein:
one or more of the plurality of biometric sensors are positioned on the rollable sleeve within a rollable portion of the rollable sleeve,
the one or more of the plurality of biometric sensors:
are positioned on an interior surface of the rollable sleeve, and
comprise an ultrasonic sensor, the ultrasonic sensor having a surface on which an acoustic matching layer is disposed; and
the rollable sleeve is configured to roll out over the limb or digit starting from an at least partially rolled up state in which at least a portion of the rollable sleeve containing the plurality of biometric sensors is at least partially rolled up defining an annular opening.

2. The biometric measuring device of claim 1, wherein the plurality of biometric sensors are positioned to further enable the plurality of biometric sensors to be in proximity with the limb or digit when the rollable sleeve is rolled out over the longitudinal axis of the limb or digit.

3. The biometric measuring device of claim 1, wherein the plurality of biometric sensors are positioned to further enable biometric information to be captured regardless of orientation of the rollable sleeve on the limb or digit.

4. The biometric measuring device of claim 1, further comprising:
a fingerprint sensor attached to the rollable sleeve at a location that enables fingerprint data of the subject to be captured when the rollable sleeve is rolled out on a digit.

5. The biometric measuring device of claim 4, further comprising a processor coupled to the fingerprint sensor and configured to:
verify an identity of the subject based on the fingerprint data captured by the fingerprint sensor; and
associate the obtained biometric measurements with the identity of the subject.

6. The biometric measuring device of claim 1, wherein the one or more of the plurality of biometric sensors include one or more pressure sensors comprising one or more of a capacitive material strip, a piezo resistive film, or a strain gauge.

7. The biometric measuring device of claim 1, wherein the rollable sleeve is made of an elastic material and at least one of the plurality of biometric sensors is embedded within the elastic material of the rollable sleeve.

8. The biometric measuring device of claim 1, wherein the rollable sleeve comprises a moulded structure and the plurality of biometric sensors are embedded in or attached to the moulded structure of the rollable sleeve.

9. The biometric measuring device of claim 1, wherein the rollable sleeve is made of a material that provides a constant counter pressure when the rollable sleeve is rolled out on the limb or digit.

10. The biometric measuring device of claim 1, wherein the rollable sleeve is waterproof.

11. The biometric measuring device of claim 1, wherein the plurality of biometric sensors further comprises an optical sensor, a pressure sensor, a bio-impedance sensor, or any combination thereof.

12. The biometric measuring device of claim 1, further comprising a processor coupled to the plurality of biometric sensors, wherein the processor is configured to determine one or more biometric measurements based on outputs received from the plurality of biometric sensors.

13. The biometric measuring device of claim 12, further comprising:
one or more transceivers coupled to the processor and configured to transmit the one or more biometric measurements to a remote device.

14. The biometric measuring device of claim 1, further comprising:
a Faraday cage attached to the rollable sleeve, wherein the Faraday cage is configured to electrically shield the plurality of biometric sensors.

15. The biometric measuring device of claim 1, wherein the plurality of biometric sensors include a row of biometric sensors forming an at least partial ring extending around a circumference of the rollable sleeve, to enable the rollable sleeve to be rolled.

16. The biometric measuring device of claim 1, wherein the plurality of biometric sensors comprises one or more pressure sensors attached to the rollable sleeve, wherein the one or more pressure sensors are configured to determine a counter pressure applied to the limb or digit by the rollable sleeve.

17. The biometric measuring device of claim 1, wherein the ultrasonic sensor comprises a thin film transistor (TFT) layer interposed between two piezoelectric film layers.

18. A method of measuring a biometric property of a subject using a biometric measuring device comprising a rollable sleeve and a plurality of biometric sensors attached to the rollable sleeve, wherein one or more of the plurality of biometric sensors are positioned on the rollable sleeve within a rollable portion of the rollable sleeve, and the one or more of the plurality of biometric sensors are positioned on an interior surface of the rollable sleeve, and comprise an ultrasonic sensor, the ultrasonic sensor having a surface on which an acoustic matching layer is disposed, and wherein the rollable sleeve is rolled out over the limb or digit starting from an at least partially rolled up state in which at least a portion of the rollable sleeve containing the plurality of biometric sensors is at least partially rolled up defining an annular opening, the method comprising:
receiving output signals from the plurality of biometric sensors attached to the rollable sleeve when the rollable sleeve is deployed on a limb or digit of the subject the output signals including output signals from the ultrasonic sensor; and
processing the output signals to obtain one or more biometric measurements.

19. The method of claim 18, wherein processing the output signals to obtain one or more biometric measurements comprises processing the output signals in a processor coupled to the plurality of biometric sensors.

20. The method of claim 18, wherein processing the output signals to obtain one or more biometric measurements comprises:
transmitting the output signals to a computing device separate from the biometric measuring device; and
processing the output signals on the computing device to obtain the one or more biometric measurements.

21. The method of claim 18, wherein the biometric measuring device includes a fingerprint sensor attached to the rollable sleeve at a location that enables fingerprint data of the subject to be captured when the rollable sleeve is deployed on a digit of the subject, the method further comprising:
capturing the fingerprint data of the subject by the fingerprint sensor when the rollable sleeve is deployed on the digit of the subject.

22. The method of claim 21, further comprising:
verifying an identity of the subject based on the fingerprint data captured by the fingerprint sensor; and
associating the obtained biometric measurements with the identity of the subject.

23. A biometric measuring device for obtaining biometric measurements on a limb or digit of a subject, comprising:
a rollable sleeve, wherein the rollable sleeve is rollable along a longitudinal axis of the limb or digit; and
a plurality of means for obtaining biometric measurements attached to the rollable sleeve, wherein:
one or more of the plurality of means for obtaining biometric measurements are positioned on the rollable sleeve within a rollable portion of the rollable sleeve,
the plurality of means for obtaining biometric measurements:
are positioned on an interior surface of the rollable sleeve, and
comprise an ultrasonic sensor, the ultrasonic sensor having a surface on which an acoustic matching layer is disposed; and
the rollable sleeve is configured to roll out over the limb or digit starting from an at least partially rolled up state in which at least a portion of the rollable sleeve containing the plurality of means for obtaining biometric measurements is at least partially rolled up defining an annular opening.

24. The biometric measuring device of claim 23, wherein the plurality of means for obtaining biometric measurements are positioned on the rollable sleeve to further enable the plurality of means for obtaining biometric measurements to be in proximity with the limb or digit when the rollable sleeve is rolled out over the longitudinal axis of the limb or digit.

25. The biometric measuring device of claim 23, further comprising:
means for capturing fingerprint data when the biometric measuring device is deployed on a digit of the subject.

26. The biometric measuring device of claim 25, further comprising:
means for verifying an identity of the subject based on captured fingerprint data; and
means for associating obtained biometric measurements with the identity of the subject.

27. The biometric measuring device of claim 23, further comprising means for determining a counter pressure applied to the limb or digit of the subject by the rollable sleeve.

28. The biometric measuring device of claim 23, wherein the rollable sleeve is made of an elastic material and the plurality of means for obtaining biometric measurements are embedded within the elastic material of the rollable sleeve.

29. The biometric measuring device of claim 23, wherein the plurality of means for obtaining biometric measurements comprise:
means for obtaining biometric measurements using light;
means for obtaining biometric measurements using ultrasound;
means for obtaining biometric measurements using bioimpedance;
or any combination thereof.

30. The biometric measuring device of claim 23, further comprising:
means for transmitting biometric measurements to a remote computing device.

* * * * *